United States Patent
Lin (10) Patent No.: US 6,697,663 B1
(45) Date of Patent: Feb. 24, 2004

(54) METHOD AND APPARATUS FOR REDUCING NOISE ARTIFACTS IN A DIAGNOSTIC IMAGE

(75) Inventor: Zhongmin Steve Lin, Solon, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 404 days.

(21) Appl. No.: 09/710,461

(22) Filed: Nov. 9, 2000

(51) Int. Cl.⁷ .............................. A61B 5/05; A61B 6/00
(52) U.S. Cl. ......................................... 600/425; 378/22
(58) Field of Search .................... 600/425, 426, 600/427, 428, 429, 407; 378/21, 22, 23, 24, 25, 26

(56) References Cited

U.S. PATENT DOCUMENTS

| | | | |
|---|---|---|---|
| 3,798,366 A | * | 3/1974 | Hunt et al. .................. 374/124 |
| 5,079,426 A | | 1/1992 | Antonuk et al. |
| 5,117,114 A | | 5/1992 | Street et al. |
| 5,164,809 A | | 11/1992 | Street et al. |
| 5,262,649 A | | 11/1993 | Antonuk et al. |
| 5,357,550 A | * | 10/1994 | Asahina et al. ............. 378/98.5 |
| 5,582,171 A | * | 12/1996 | Chornenky et al. .......... 600/425 |
| 5,748,768 A | * | 5/1998 | Sivers et al. ................ 382/130 |
| 6,031,891 A | | 2/2000 | Roos et al. |
| 6,192,265 B1 | * | 2/2001 | Carlsen et al. .............. 600/425 |
| 6,263,231 B1 | * | 7/2001 | Reitter ........................ 600/425 |
| 6,421,552 B1 | * | 7/2002 | Hsieh ......................... 600/425 |

* cited by examiner

Primary Examiner—Thomas Denion
Assistant Examiner—Daniel Robinson
(74) Attorney, Agent, or Firm—Fay, Sharpe, Fagan, Minnich & McKee, LLP (57) ABSTRACT

A The medical diagnostic imaging apparatus includes a source (12) for generating x-rays, an image receptor (26) for receiving the x-rays and generating image data, and an image processing subsystem (6) for generating corrected image data from the image data acquired by the image receptor. The image processing subsystem includes a processor (46) that is programmed to generate noise image data (54) by high-pass filtering (52) uncorrected diagnostic image data acquired by the image receptor, to determine statistical data (64, 66) from a first subset (56) of the noise image data, and to correct a subset (36) of the uncorrected diagnostic image data based on the statistical data, the subset of the uncorrected diagnostic image data corresponding to the subset of the noise image data.

22 Claims, 4 Drawing Sheets

METHOD AND APPARATUS FOR REDUCING NOISE ARTIFACTS IN A DIAGNOSTIC IMAGE

BACKGROUND OF THE INVENTION

The present invention relates to the medical diagnostic imaging arts. It finds particular application in conjunction with a method and apparatus for reducing, suppressing, and/or eliminating noise and/or other image artifacts that are present in a diagnostic image that is generated by a flat panel image receptor of a diagnostic imaging system, and will be described with particular reference thereto. However, it should be appreciated that the present invention may also find application in conjunction with other types of imaging systems and applications where reducing noise and other image artifacts is desired.

The sensitivity of x-ray image detector devices, including flat panel image sensors or receptors, is limited by noise, i.e., random signal fluctuations that compete with data or other information that represents or otherwise defines a captured image. One type of noise that is characteristic of some flat panel image receptors, such as amorphous Silicon-based, flat panel image receptors, is line-correlated noise. Line-correlated noise can be defined as random fluctuations that affect a whole raster line of a video frame in a manner that causes all the picture elements ("pixels") of a raster line to commonly deviate from their actual captured image values.

The manifestation of line correlated-noise in a video image displayed on a video monitor is stripes that fluctuate in intensity across the width of the image. This is an undesirable effect that is highly distracting to medical personnel, such as physicians, when using a diagnostic imaging system, such as a fluoroscopic, radiographic, computed tomographic (CT), magnetic resonance (MR) imaging system, nuclear camera, etc., to perform interventional procedures.

There are known image processing techniques, generally referred to as blacklevel clamping or line noise clamping, for reducing the amount of line-correlated noise generated in image receptors. These techniques rely on one or more clamp or reference zones formed from corresponding strips of radiation impervious material such as lead. The clamp or reference zones are positioned along either one or both vertical side edges of an image receptor active area (i.e. perpendicular to the image raster lines) in front of corresponding radiation sensors. The clamp or reference zones effectively black-out or prevent the corresponding radiation sensors from receiving or capturing any x-ray radiation generated by an x-ray source. Thus, the radiation sensors are prevented from generating image information, and should give a zero output, but for noise.

The blacked-out reference zones are each a predetermined number of pixels wide. The only output signals or information received from the pixels within the blacked-out reference zones is random noise and line-correlated noise—the same line noise that affects the pixels in the exposed or active region of the image receptor.

Line noise cancellation involves determining the average output value of the reference pixels within the blacked-out zones for each raster line of each video frame to average out the random noise fluctuations of each reference pixel, and to yield the error introduced in that particular raster line by line noise alone. The resulting error value is then uniformly subtracted from each of the active area pixels in the corresponding raster line prior to being displayed on a video monitor.

The known blacklevel or line noise clamping techniques are hardware dependent. That is, the known clamping techniques require modifications/enhancements to an active area of the associated flat panel image receptor (e.g. providing lead strips on one or both vertical edges of the active area associated with a flat panel image detector). Although the lead strip technique works well for smaller detectors, it is not readily adapted to large detectors.

Accordingly, it is considered desirable to develop a new and improved method and apparatus for reducing noise artifacts in a diagnostic image, which method is hardware-independent (i.e. not a detector-related accessory), that meets the above-stated needs and overcomes the foregoing difficulties and others while providing better and more advantageous results.

SUMMARY OF THE INVENTION

In accordance with one aspect of the present invention, a method for generating corrected diagnostic image data is disclosed. The method includes a) acquiring uncorrected diagnostic image data from x-rays generated by an x-ray source; b) filtering the uncorrected diagnostic image data to generate noise image data; c) determining statistical data from a first subset of the noise image data; and d) correcting a second subset of the uncorrected image data based on the statistical data, the second subset of the uncorrected image data corresponding to the first subset of the noise image data.

In accordance with another aspect of the present invention, a medical diagnostic imaging apparatus is disclosed. The apparatus includes a source for generating x-rays, an image receptor for receiving the x-rays and generating image data, and an image processing subsystem for generating corrected image data from the image data acquired by the image receptor. The image processing subsystem includes a processor programmed to a) high-pass filter the image data acquired by the image receptor to generate high-pass filtered image data; b) select a region of interest from a plurality of regions of interest within the high-pass filtered image data, the region of interest comprising a plurality of first raster line segments; c) determine an integration value for each of the plurality of raster line segments; d) determine an average integration value for the region of interest; e) determine an error value for a selected one of the plurality of first raster line segments, the error value based on the integration value for the selected one of the plurality of first raster line segments and on the average integration value; and f) determine a noise-corrected pixel value for a pixel associated with a second raster line segment associated with the image data acquired by the image receptor, the second raster line segment corresponding to the selected one of the plurality of first raster line segments associated with the high-pass filtered image data.

In accordance with yet another aspect of the present invention, an apparatus for generating corrected diagnostic image data is disclosed. The apparatus includes a mechanism for acquiring uncorrected diagnostic image data from x-rays generated by an x-ray source; a mechanism for filtering the uncorrected diagnostic image data to generate noise image data; a mechanism for determining statistical data from a first subset of the noise image data; and a mechanism for correcting a second subset of the uncorrected image data based on the statistical data, the second subset of the uncorrected image data corresponding to the first subset of the noise image data.

One advantage of the present invention is the provision of a method and apparatus that reduces noise artifacts in a diagnostic image by extracting line fluctuations (i.e. noise) directly from image data generated from an x-ray detector.

Another advantage of the present invention is the provision of a method and apparatus that reduces noise artifacts in a diagnostic image using high pass filtering and data fitting techniques to extract line noise fluctuations.

Yet another advantage of the present invention is the use of a method and apparatus that reduces noise artifacts in selected regions of interest of a diagnostic image.

Still another advantage of the present invention is the use of a method and apparatus that reduces noise artifacts in a diagnostic image by providing a mechanism that optimizes the filtering of line noise from diagnostic image data.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment(s) and are not to be construed as limiting the invention.

DETAILED DESCRIPTION OF THE PREFERRED EMBODIMENT(S)

Figure 1:
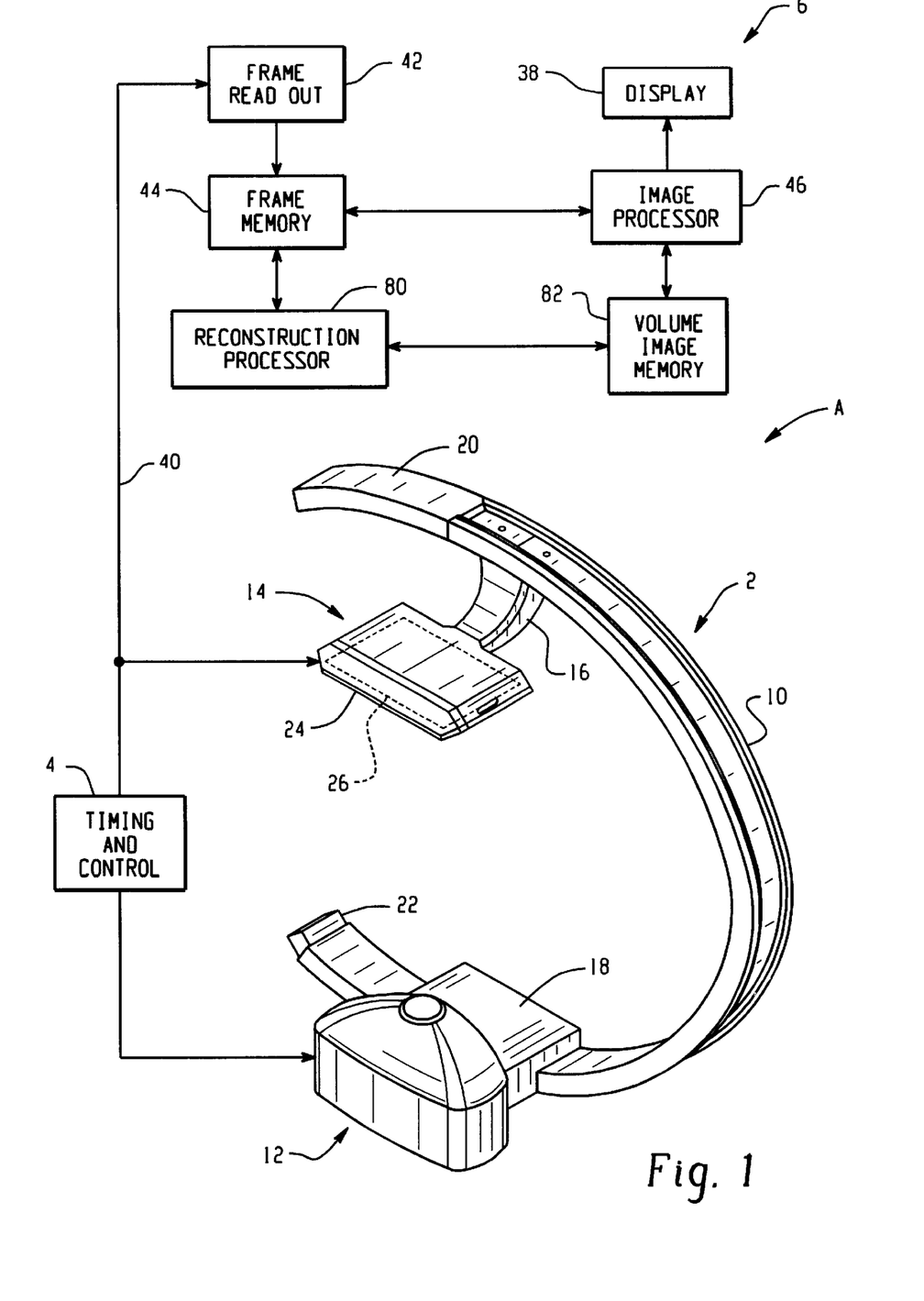
FIG. 1 is a diagrammatic view of an exemplary diagnostic imaging system that incorporates the features of the present invention therein.

With reference to FIG. 1, an exemplary diagnostic imaging system A includes an image data acquisition subsystem 2, a timing and control subsystem 4, and a image processing subsystem 6. The image data acquisition subsystem 2 includes, but is not limited to, a support member 10, such as a closed ring, C-arm, etc. having an x-ray source 12 and an x-ray detector 14 secured thereto. In the embodiment being described, the support member 10 is a C-arm, and the x-ray source 12 and detector 14 are secured proximate opposing ends of the C-arm via cantilevered support brackets 18, 16, respectively. The C-arm can be counterbalanced with upper and lower counterweights 20, 22 extending from the respective ends of the C-arm. The detector 14 includes a housing 24 which supports a flat panel image receptor or array of image receptors 26.

Figure 2:
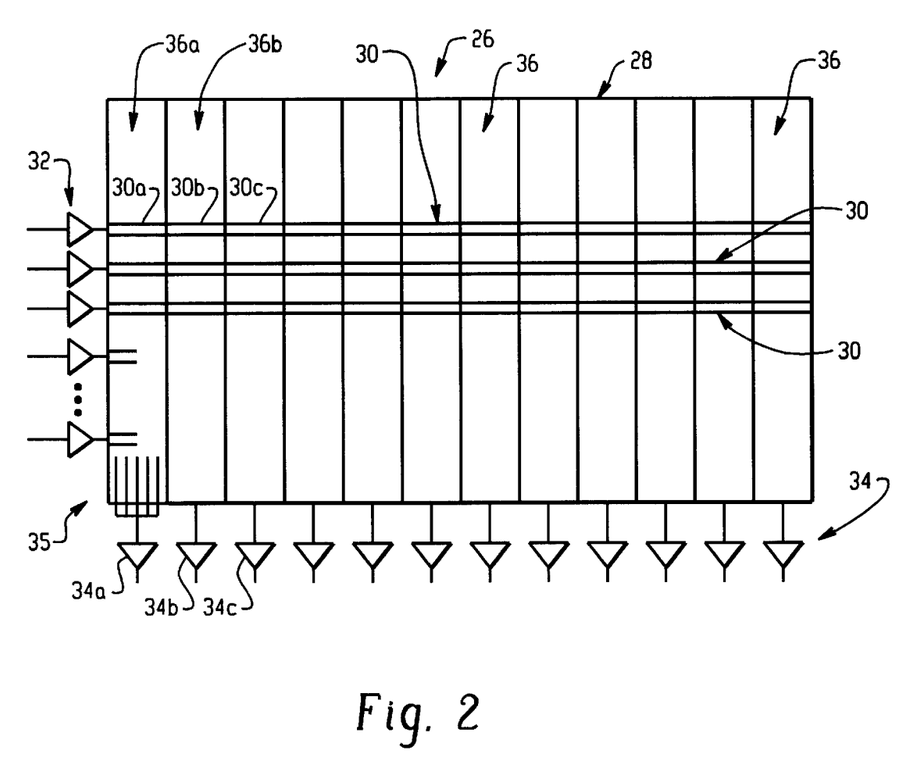
FIG. 2 is a diagrammatic view of a flat panel image receptor associated with the diagnostic imaging system of FIG. 1.

With reference to FIG. 2, an active area or region 28 of the flat panel image receptor 26 comprises a plurality of rows or raster lines 30 extending across the active area 28 in a first direction. In the embodiment being described, the active area 28 has a width of 768 pixels, cells, or detector elements in the first direction, and a height of 960 pixels, cells, or detector elements in a second direction perpendicular to the first direction. A series of drivers 32 drive detector elements associated with corresponding raster lines 30. A series of amplifiers 34 amplify signals from the detector elements in a series of columns 35 extending down the active area 28 in the second direction transverse to the first. The columns are generally grouped into regions 36 such that a first amplifier 34a amplifies signals from the detector elements within the region 36a, a second amplifier 34b amplifies signals from the detector elements within the region 36b, etc. In the embodiment being described, the columns 35 are grouped into twelve regions 36. The signals acquired from the detector elements are read out in lines parallel to the driver rows 30. Thus, each raster line of data 30 is divided into sections or segments 30a, 30b, 30c, etc. which have the noise characteristics of each of the corresponding drivers 32 and amplifiers 34. Typically, the noise associated with each amplifier 34a–34c is different, thus rendering conventional black level clamping techniques, that operate on each raster line as a whole, inaccurate.

The active area or region 28 of the flat panel image receptor 26 is generally formed from a planar substrate such as glass laminated with an array of sensors such as amorphous Silicon crystals. The flat panel image receptor 26 can utilize direct x-ray detection whereby x-rays are absorbed in a semi-conductor matrix, such as Selenium, Lead Sulfide, Cadmium Zinc Telluride, or Lead Iodide, and then converted directly to an electrical charge which is then accumulated by the amorphous Silicon matrix. Alternatively, the flat panel image receptor 26 can utilize indirect x-ray detection whereby x-rays are absorbed in a scintillating phosphor layer, such as Gadolinium Oxysulfide, Cesium Iodide, or Cadmium Tungstate, and then converted to light. An array of photodiodes on the glass substrate convert the light into electrical signals.

In either case, the electrical signals are readout of a row/column matrix that is accessed using thin film transistor switches on the amorphous Silicon substrate. The analog image data is then converted to a digital format by suitable analog-to-digital (A/D) circuitry associated with the detector 14 and/or the image processing subsystem 6. Suitable amorphous Silicon-based flat panel detectors are described, for example, in U.S. Pat. Nos. 5,079,426; 5,117,114; 5,164,809; and 5,262,649.

Referring again to FIG. 1, the timing and control subsystem 4 causes a conventional power supply associated with the x-ray source 12 to pulse at radiographic energy levels in a radiographic mode of operation, or at fluoroscopic energy levels in a fluoroscopic mode of operation. The x-ray source 12 sends a pulse of x-rays for a limited duration through the subject striking the flat panel image receptor 26. Due to the low fluoroscopic energy levels in the fluoroscopic mode of operation, each cell of the flat panel image receptor 26 integrates received radiation over the duration of the pulse.

The flat panel image receptor 26 constitutes an input component to the image processing subsystem 6. The image processing subsystem 6 generally assembles and transmits an acquired or captured image, or a sequence of images (in the case of fluoroscopy imaging), to one or more display devices such as a video monitor 38. In addition, the subsystem 6 can employ conventional scan converters for the image data so as to, for example, transmit assembled images to a laser transparency printer for radiographic recording, or to electronically store the media for archival purposes. The radiographic images that have been transferred to film can be displayed on a radiography viewing device such as a conventional light box.

The image processing subsystem 6 receives analog and/or digital image data from the image receptor 26 or other upstream imaging process, in a standard raster pattern accompanied by frame, line, and/or pixel synchronization signals on one or more data and/or control lines 40 (shown schematically as a single line) from the image detector 14 and/or the timing and control subsystem 4. That is, after a radiation pulse is generated by the x-ray source 12, the timing and control subsystem 4 causes a frame read out circuit 42 of the image processing subsystem 6 to read out the two-dimensional frame image data generated or captured by the flat panel image receptor 26, and then to store the frame image data in a frame buffer or memory 44. It should be appreciated that the captured frame image data that is stored as an array in the frame memory 44 can include line noise from various sources such as the input power line, driver lines, and ASIC (i.e. drivers 32 and/or amplifiers 34) interference. The line noise is generally manifested as sharp fluctuations in the magnitudes of the digital data representing the stored frame image.

An image processor or controller 46 addresses (i.e. reads data from and writes data to) the frame memory 44. The image processor 46 includes conventional circuitry that i) executes a routine that reduces, suppresses, and/or eliminates noise and/or other high-frequency image artifacts that are present in the original frame image, and ii) retrieves a noise-corrected frame image from the frame memory 44 for display on the video monitor 38.

Figure 3:
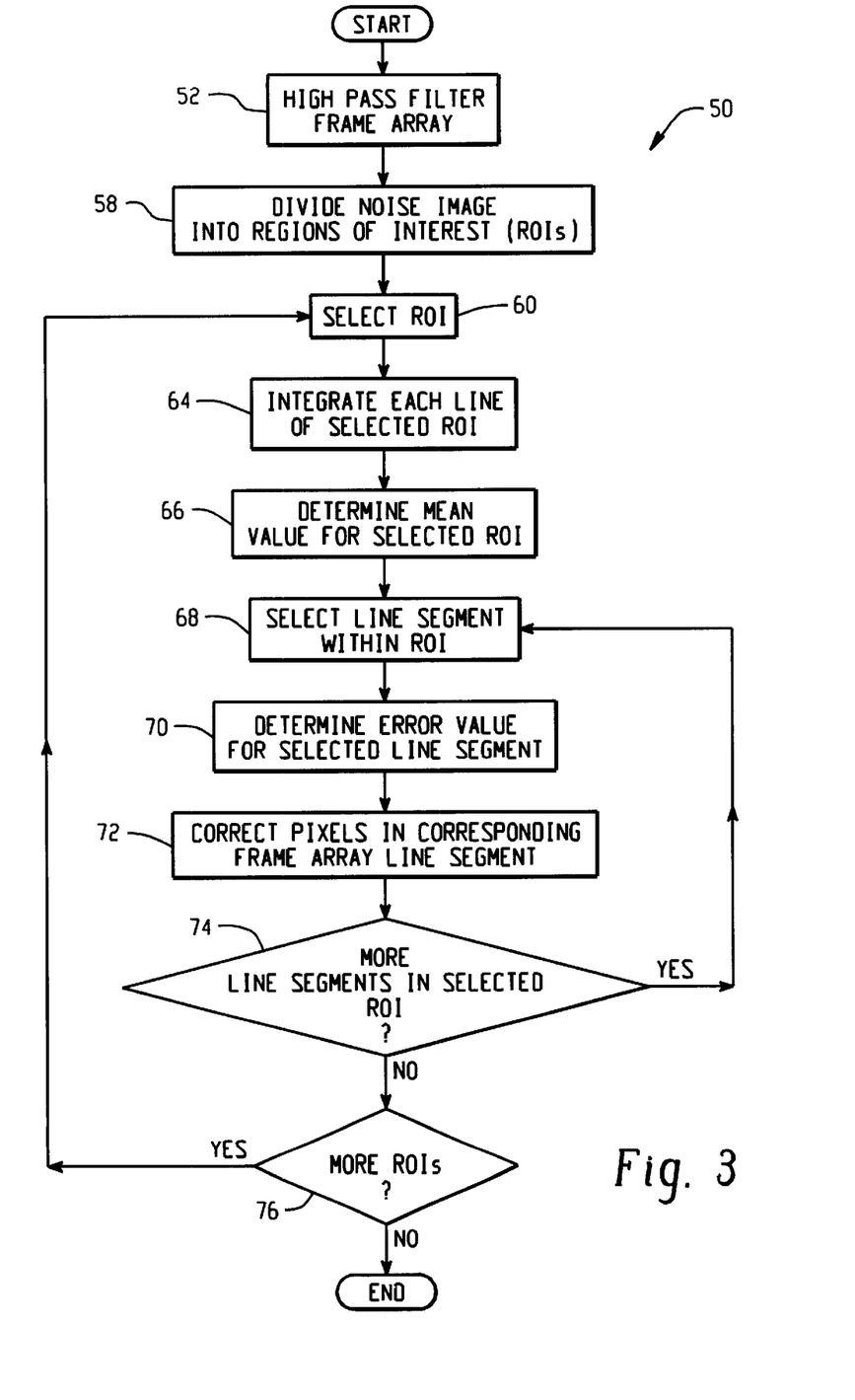
FIG. 3 is a flow chart illustrating a method for reducing noise artifacts in diagnostic images generated by the diagnostic imaging system of FIG. 1.

Referring now to FIG. 3, the noise correction routine 50 of the present invention begins by bit or pixel-wise high-pass filtering the digital data comprising the original frame image (step 52). It should be appreciated that the digital image data can be conventionally high-pass filtered in either the frequency domain or the spatial domain to remove the low-frequency components of the frame image. The resulting array of high-pass filtered digital data 54 (FIG. 4) represents a high-frequency or noise image that contains high-frequency signals and high-frequency noises, including any line noise that may be present.

For example, a spatial domain or area processing technique such as convolution uses an original, input, or source pixel value (e.g. a frame image pixel) as well as the pixel values around it to generate a corrected (i.e. high-pass filtered) or output pixel value (i.e. a noise image pixel). A convolution is merely a weighted sum of pixel values in a neighborhood surrounding the input pixel. The weights are determined by a small matrix referred to as the convolution mask or convolution kernal. The dimensions of the matrix are usually odd (e.g. 3×3, 5×5, etc.) so that a center pixel of the matrix is present. The matrix center pixel corresponds to an output pixel that is generated as a result of the high-pass filtering step.

A sliding window, referred to as the convolution window, centers on each pixel in the original frame image and pixel-wise generates new high-pass filtered output pixel values. The new pixel values are each computed by multiplying each original pixel value in the neighborhood with the corresponding weight in the convolution mask and summing these products. The new or output pixel values are stored separately from the original pixel values within the frame buffer or memory 44. By way of example, a suitable 3×3 convolution mask with corresponding coefficients for high-pass filtering the original frame image is:

| −1/9 | −1/9 | −1/9 |
| −1/9 | 8/9 | −1/9 |
| −1/9 | −1/9 | −1/9 |

Thus, the result of the high-pass filtering step 52 is to generate a high-pass filtered or high-frequency noise image 54 (FIG. 4) that is separate from the original frame image.

Figure 4:
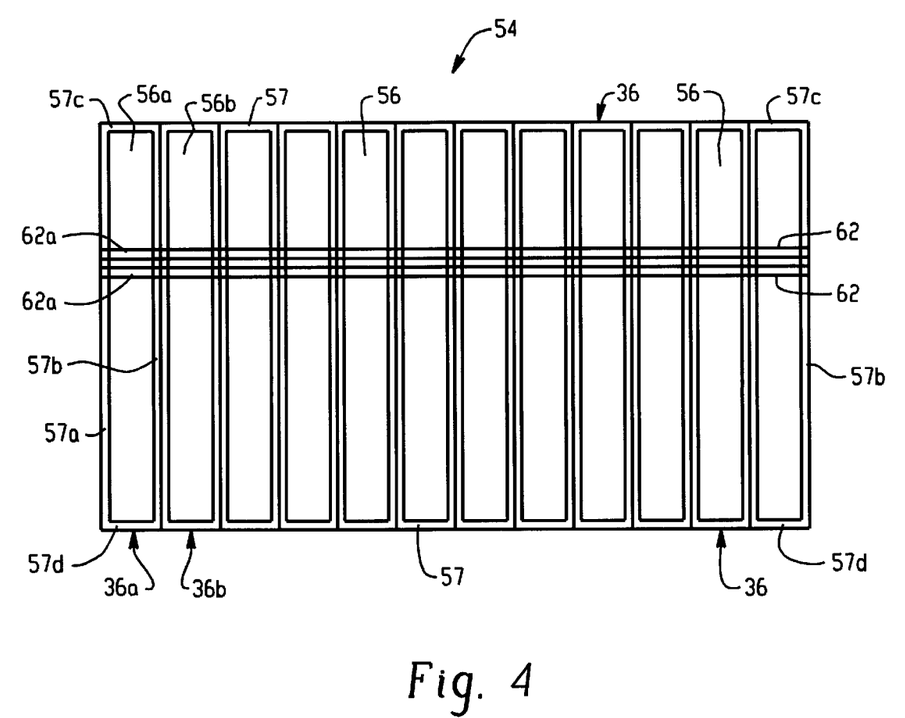
FIG. 4 is a simplified data buffer or frame image memory with an array of image data stored therein.

With continued reference to FIG. 4, the resulting noise image 54 is then divided into several regions of interest (ROIs) 56 (step 58). In the embodiment being described, each ROI 56 corresponds to a subregion of a corresponding amplifier region 36. That is, ROI 56a is or forms a subregion of amplifier region 36a, ROI 56b forms a subregion of amplifier region 36b, etc. In such a case, the pixels or pixel data defining a boundary 57 of a given region 36 do not form part of the corresponding subregion 56. For example, if a given region 36a is about 64 pixels wide, then the corresponding subregion 56a may only be about 52 to about 58 pixels wide, with first and second vertical borders 57a, 57b, each being about 3 to about 7 pixels wide. Further, if the region 36a is about 960 pixels or rows high, then the corresponding subregion 56a may only be about 940 to about 950 pixels high, with first and second horizontal borders 57c, 57d, each being about 5 to about 10 pixels high.

A subregion 56 is then selected for further processing (step 60). Line integration is performed on each line segment 62 (FIG. 4) within the selected subregion 56 (step 64). That is, the pixel values within a given line segment 62 are summed together to determine a line integration value for the given line segment 62. The integrated line signals are then analyzed and statistical data, such as standard deviation, mean value, etc., are determined. For example, a mean or average value for the subregion 56 is determined by summing all of the line integration values for the selected subregion 56 together and then dividing the result by the number of line segments 62 within the selected subregion 56 (step 66). The integrated line signals and noises are then fitted to a base function. In most diagnostic imaging applications, the base function is simply a straight line of the mean value or a slowly varied signal. The fluctuation of the integrated line noises are then determined. In particular, a line segment 62 of the subregion 56 is selected (step 68), and then a line noise amplitude or error value for the selected line segment 62 is determined (step 70). A larger line noise amplitude value represents a line segment with more noise than a line segment with a smaller value. In the embodiment being described, the line noise amplitude value ERR can be determined by calculating the absolute difference between the line integration value LINT for the selected line segment 62 and the mean value AVG determined in step 66. That is, $$ERR = |LINT - AVG| \tag{1}$$

The line noise amplitude value for the selected line segment 62 is then used to correct the pixel data of the corresponding line segment 30 in the amplifier region 36 of frame array 28 (step 72). That is, the line noise amplitude value ERR for a selected line segment 62 is subtracted from each pixel value $P_{orig}$ of the corresponding line segment 30 in the amplifier region 36 of the frame array 28 to generate a noise-corrected output pixel $P_{corr}$. That is, $$P_{corr} = P_{orig} - ERR \tag{2}$$

The noise-corrected pixel value $P_{corr}$ can either replace the original pixel value $P_{orig}$, or can be stored in a new memory location within a memory, such as frame memory 44, to create a separate noise-corrected image.

Alternatively, it is contemplated that threshold and/or scale values can be used to optimize the suppression of line noise. For instance, each pixel value $P_{orig}$ of the corresponding line segment 30 in the amplifier region 56 of the frame array 28 can be corrected according to:

$$P_{corr} = P_{orig} - (ERR)(RATIO) \tag{3}$$

where $P_{corr}$ is the resulting noise-corrected pixel value, $P_{orig}$ is the original pixel value, ERR is the error value for the selected line segment 62, and RATIO is a scale value that is used to optimize line noise suppression.

In the embodiment being described, RATIO can be within the range of about 0.5 to about 1.5, and is the same for the whole frame image. However, the value for RATIO can be adjusted accordingly in cases where image data within a particular ROI is particularly noisy. That is, Eq. 3 provides a mechanism for optimizing the elimination of the line noises by varying threshold or scale values to achieve the best noise suppression or filtering.

Thereafter, it is determined whether or not each of the line segments 62 of the selected ROI 56 have been parsed (step 74). Steps 68–74 are repeated for each line segment 62 in the selected ROI 56. Thereafter, it is determined whether or not each of the ROIs 56 have been parsed (step 76). Steps 60–76 are repeated for each ROI 56. When all of the ROIs 56 have been parsed, the result is a noise-corrected diagnostic image that is stored in the frame memory 44, and that can be addressed by the image processor 46 for viewing on the display 38.

Referring again to FIG. 2, it is contemplated that the x-ray source 12 and detector 14 can be positioned within or proximate a bore of a diagnostic imaging apparatus such as a CT scanner, nuclear camera, etc. In this case, a drive motor (not shown) can be used to index the x-ray source 12 and flat panel detector 14 to selectable angular orientations around a central axis of the support member 10. A patient table or support (not shown) can be used to position the subject to be imaged at the geometric center of the support member 10. The timing and control subsystem 4 can be modified to also control the drive motor to index the x-ray source and detector to each of a plurality of pre-selected angular positions around the subject, e.g., steps at 1° intervals. At each step, the timing and control subsystem 4 causes the x-ray source power supply to pulse the x-ray tube at radiographic energy levels in a radiographic mode of operation, and fluoroscopic energy levels in a fluoroscopic mode of operation. The x-ray tube sends a pulse of x-rays for a limited duration through the subject striking the flat panel detector 26.

After the radiation pulse, the timing and control subsystem 4 causes the frame read out circuit 42 to read out the two dimensional frame image generated by the flat panel detector 26 in the manner described above. Concurrently, the timing and control subsystem 4 causes the drive motor to index the x-ray source 12 and flat panel detector 14 to the next angular step.

This process is repeated to collect a plurality of two dimensional frame images each of which are collected in the frame memory 44. Each frame image represents a two dimensional array of image data that represents radiation attenuation along a corresponding ray through the patient. Because the x-ray tube 12 is essentially a point source which generates rays of diverging radiation directed toward the flat panel receptor 26, each ray represents the attenuation of radiation along one of a plurality of diverging paths. The paths diverge generally in a cone beam pattern.

Accordingly, after the image processor 46 has corrected (e.g. reduced, suppressed, or eliminated) noise artifacts from each of the plurality of frame images in the manner described above, a reconstruction processor 80 can be used to reconstruct each corrected frame of data and use it to improve a three dimensional volumetric image that is assembled and stored in a volumetric image memory 82. With each frame that is reconstructed and combined into the volumetric image representation, the volumetric image becomes clearer and sharper. Preferably, the x-ray source and flat panel detector rotate at least 180° plus the angle of the cone beam and the rotational direction around the subject.

The image processor 46 addresses the volume image memory 82 to retrieve slices, projections, 3-D renderings, and other conventional diagnostic image display formats such as Maximum Intensity Projection images (MIP), etc. The reconstruction processor 80 and/or image processor 46 can include means, such as an algorithm, to compensate the image data for image lag caused by the scintillator layer and the amorphous silicon matrix if an optical reset device is not used. Further, the reconstruction processor 80 and/or image processor 46 can also perform any image data corrections that are specific to the type of flat panel image receptor being used. In the case of an amorphous Silicon flat panel detector 26, this includes at least the following processes: pixel offset correction, pixel gain correction, defective pixel interpolation and blacklevel clamping (i.e. line correlated noise reduction). Lastly, it is appreciated that the image processor 46 and reconstruction processor 80 can be individual processors, or can be combined to form a single processor that is programmed to perform multiple processing functions.

Thus, the present invention passes the image data generated by the detector 14 through a high-frequency filter to generate a high-frequency image, i.e., a noise image. This noise image is then analyzed for areas of different noise characteristics, or is automatically divided into regions corresponding to the amplifiers. In any case, the line segments within each region are averaged and adjusted for a baseline function. Each line segment is then subtracted from the average to provide an indication of its relative noisiness. This indication of relative noisiness of each line segment is used to adjust the count at each-pixel of the corresponding data line segment.

The baseline function adjustment adjusts for the expected zero or baseline value across each region. That is, the subject which is imaged can add noise, particularly at regions of sharp discontinuities. Because the human body typically has no sharp discontinuities in the image, in most cases, the baseline function can be estimated as a straight line for medical diagnostic imaging. In this manner, the noise characteristics of the image itself is used to make a noise correction which eliminates the line noise artifacts. Thus, there is no need for other detector accessories, such as lead covered edges, etc.

The present invention more effectively filters out line noises because it extracts line noise fluctuations directly from the image to be corrected. As discussed above, the causes of the flat panel line noise are very complicated. Trying to simply use dark field signals from a fixed lead-covered area may miss other causes such as the influence of the amplifiers and the pixel fluctuation. For such a sophisticated random phenomena, the best way to extract the line noises without missing other unknown causes is to correct the image data itself. The present invention works not only on the whole line noises but also works on the segments of line noises. The invention extracts line noises according to the most distinguished feature of the image.

The invention has been described with reference to the preferred embodiment(s). Obviously, modifications and alterations will occur to others upon reading and understanding the preceding detailed description. It is intended that the invention be construed as including all such modifications and alterations insofar as they come within the scope of the appended claims or the equivalents thereof.

For instance, it should be appreciated that the present method and apparatus for reducing noise artifacts in a diagnostic image can be implemented in hardware, software, firmware, or any combination thereof. In addition, specific reference is made to correcting for line correlated noise associated with an amorphous Silicon flat panel receptor. However, it is contemplated that the present method and apparatus for reducing noise artifacts in a diagnostic image is applicable with other image receptors in the medical and electronic imaging arts.

Having thus described the preferred embodiments, the invention is now claimed to be:

1. A medical diagnostic imaging apparatus including an upstream rasterized imaging processor that generates rasterized uncorrected image data, and a processing means for generating corrected image data from the rasterized uncorrected diagnostic image data, the processing means being programmed to:
   a) filter the uncorrected diagnostic image data to generate noise image data;
   b) determine statistical data from a first subset of the noise image data, the determining including:
      determining integration values for each of a plurality of raster line segments within a region of interest,
      determining an average integration value for the region of interest, and
      determining a line noise amplitude factor for a selected raster line segment within the region of interest based on the integration value of the selected raster line segment and the average integration value; and
   c) correct a second subset of the uncorrected diagnostic image data based on the statistical data, the second subset of the uncorrected diagnostic image data corresponding to the first subset of the noise image data.

2. The apparatus of claim 1, wherein the processing means is further programmed to:
   d) repeat b) and c) for additional subsets of the noise image data.

3. The apparatus of claim 2, wherein the processing means is further programmed to:
   e) generate a volumetric image representation from the corrected diagnostic image data.

4. The apparatus of claim 2, further comprising:
   a means for displaying a two-dimensional image representation of the corrected diagnostic image data.

5. The apparatus of claim 1, wherein a) includes:
   high-pass filtering the uncorrected diagnostic image data to generate the noise image data.

6. A medical diagnostic imaging apparatus including a means for generating x-rays, a flat panel image receptor for receiving the x-rays and g generating uncorrected electronic image data, and a processing means for generating corrected image data from the uncorrected diagnostic electronic image data, the processing means being programmed to:
   a) filter the uncorrected diagnostic electronic image data to generate noise image data;
   b) determine statistical data from a first subset of the noise image data; and
   c) correcting a second subset of the uncorrected diagnostic electronic image data based on the statistical data, the second subset of the uncorrected diagnostic electronic image data corresponding to the first subset of the noise image data.

7. The apparatus of claim 6, wherein the processing means is further programmed to:
   divide the noise image data into a plurality of subsets corresponding to a plurality of amplifier regions associated with the flat panel image receptor.

8. A medical diagnostic imaging apparatus including a means for generating x-rays, a means for receiving the x-rays and generating uncorrected image data, and a processing means for generating corrected image data from the uncorrected diagnostic image data, the processing means being programmed to:
   a) filter the uncorrected diagnostic image data to generate noise image data;
   b) determine statistical data from a first subset of the noise image data, the determining including:
      selecting a region of interest from a plurality of regions of interest within the noise image data, the region of interest comprising a plurality of first raster line segments,
      determining an integration value for each of the plurality of first raster line segments,
      determining an average integration value for the region of interest, and
      determining a line noise amplitude value for a selected one of the plurality of first raster line segments, the line noise amplitude value based on the integration value for the selected one of the plurality of first raster line segments and on the average integration value; and
   c) correcting a second subset of the uncorrected diagnostic image data based on the statistical data; the second subset of the uncorrected diagnostic image data corresponding to the first subset of the noise image data.

9. The apparatus of claim 8, wherein c) includes:
   determining a noise-corrected pixel value for a selected pixel of a plurality of pixels defining a second raster line segment associated with the uncorrected diagnostic image data, the second raster line segment corresponding to the selected one of the plurality of first raster line segments.

10. The apparatus of claim 9, wherein the processing means is further programmed to:
    repeat the determining of a noise-corrected pixel value for each of the plurality of pixels associated with the second raster line segment.

11. The apparatus of claim 10, wherein the processing means is further programmed to:
    repeat the determining of a line noise amplitude value and the determining of a noise-corrected pixel value for each of the plurality of pixels associated with the second raster line segment for each of the plurality of first raster line segments.

12. The apparatus of claim 11, wherein the processing means is further programmed to:
    repeat the determining of an integration value, the determining of an average integration value, the determining of a line noise amplitude value, and the determining of a noise-corrected pixel value for each of the plurality of pixels associated with each of the plurality of first raster line segments for each of the plurality of regions of interest.

13. A medical diagnostic imaging apparatus including a source for generating x-rays, an image receptor for receiving the x-rays and generating image data, and an image processing subsystem for generating corrected image data from the image data produced by the image receptor, the image processing subsystem including a processor programmed to:
    a) high-pass filter the image data from the image receptor to generate high-pass filtered image data;

b) select a region of interest from a plurality of regions of interest within the high-pass filtered image data, the region of interest comprising a plurality of first raster line segments;

c) determine an integration value for each of the plurality of raster line segments;

d) determine an average integration value for the region of interest;

e) determine an error value for a selected one of the plurality of first raster line segments, the error value based on the integration value for the selected one of the plurality of first raster line segments and on the average integration value; and f) determine a noise-corrected pixel value for a pixel associated with a second raster line segment associated with the image data from the image receptor, the second raster line segment corresponding to the selected one of the plurality of first raster line segments associated with the high-pass filtered image data.

14. The apparatus of claim 13, wherein the processor is further programmed to:

g) repeat f) for each pixel associated with the second raster line segment.

15. The apparatus of claim 14, wherein the processor is further programmed to:

h) repeat e) through g) for each of the plurality of first raster line segments.

16. The apparatus of claim 15, wherein the processor is further programmed to:

i) repeat b) through h) for each of the plurality of regions of interest.

17. The apparatus of claim 13, wherein the processor is further programmed to:

g) subdivide the image data acquired by the image receptor into the plurality of subregions, the plurality of subregions corresponding to a plurality of amplifier regions associated with the image receptor.

18. An apparatus for generating corrected diagnostic image data, the apparatus comprising:

a two-dimensional image receptor, means for generating uncorrected two-dimensional diagnostic electronic image data from generating radiation;

filter means for filtering the uncorrected diagnostic electronic image data to generate noise image data;

a means for determining statistical data from a first subset of the noise image data; and a means for correcting a second subset of the uncorrected diagnostic electronic image data based on the statistical data, the second subset of the uncorrected image data corresponding to the first subset of the noise image data.

19. The apparatus of claim 18, further comprising:

a means for generating at least one of a volumetric image representation and a two-dimensional image representation from the corrected diagnostic image data; and monitor for displaying the at least one of a volumetric image representation and a two-dimensional image representation.

20. The apparatus of claim 18 wherein the filter means performs high pass filtering.

21. The apparatus of claim 19 wherein the determining means, the correcting means, and the generating means are one of:

a single programmable computer; and multiple processing modules.

22. A medical diagnostic imaging apparatus comprising:

a means for generating uncorrected image data;

a filtering means for separating the uncorrected image data into noise data and filtered image data;

a means for generating a noise map from the noise data, which noise map is indicative of relative noise in subregions of the uncorrected image data from the noise data;

a means for generating an electronic image representation from the filtered image data;

a means for correcting one of the filtered image data and the electronic image representation with the noise map.

* * * * *